(12) United States Patent
Muyari et al.

(10) Patent No.: US 10,226,267 B2
(45) Date of Patent: Mar. 12, 2019

(54) TREATMENT INSTRUMENT

(71) Applicant: OLYMPUS CORPORATION, Tokyo (JP)

(72) Inventors: Yuta Muyari, Tokyo (JP); Akane Yasukawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/497,260

(22) Filed: Apr. 26, 2017

(65) Prior Publication Data

US 2017/0224365 A1 Aug. 10, 2017

Related U.S. Application Data

(63) Continuation of application No. PCT/JP2015/081303, filed on Nov. 6, 2015.

(30) Foreign Application Priority Data

Mar. 13, 2015 (JP) .................... 2015-051290

(51) Int. Cl.
*A61B 17/221* (2006.01)
*A61B 17/3205* (2006.01)
*A61B 18/14* (2006.01)
*A61B 18/00* (2006.01)

(52) U.S. Cl.
CPC ...... *A61B 17/221* (2013.01); *A61B 17/32056* (2013.01); *A61B 2017/2212* (2013.01); *A61B 2018/00601* (2013.01); *A61B 2018/141* (2013.01); *A61B 2018/1475* (2013.01)

(58) Field of Classification Search
CPC ...................... A61B 17/221; A61B 2017/2212
USPC ........................................... 606/113
See application file for complete search history.

(56) References Cited

U.S. PATENT DOCUMENTS

| 3,805,791 A | 4/1974 | Seuberth et al. |
| 5,059,199 A * | 10/1991 | Okada ............ A61B 17/221 606/127 |
| 6,152,922 A | 11/2000 | Ouchi |

(Continued)

FOREIGN PATENT DOCUMENTS

| EP | 1 849 426 A2 | 10/2007 |
| JP | H08-071082 A | 3/1996 |

(Continued)

OTHER PUBLICATIONS

International Search Report dated Dec. 28, 2015 issued in PCT/JP20151081303.

(Continued)

*Primary Examiner* — Diane Yabut
*Assistant Examiner* — Majid Jamialahmadi
(74) *Attorney, Agent, or Firm* — Scully, Scott, Murphy & Presser, P.C.

(57) ABSTRACT

A treatment instrument is that a maximum dimension of the loop portion in a direction orthogonal to the longitudinal axis in a state where half of a total length of the loop portion in a direction of the longitudinal axis of the loop portion is pulled into the sheath is 40% to 60% of a maximum dimension of the loop portion in the orthogonal direction in a state where the whole loop portion protrudes from a distal end of the sheath.

5 Claims, 6 Drawing Sheets

(56) References Cited

U.S. PATENT DOCUMENTS

2002/0091394 A1* 7/2002 Reynolds ......... A61B 17/00234
                                                    606/127
2004/0236351 A1* 11/2004 Yanuma ............... A61B 17/221
                                                    606/127
2005/0085808 A1    4/2005 Nakao

FOREIGN PATENT DOCUMENTS

| JP | H11-056864 A | 3/1999 |
| JP | H11-123198 A | 5/1999 |
| JP | 2000-041996 A | 2/2000 |
| JP | 2000-083964 A | 3/2000 |
| WO | 2009/011721 A1 | 1/2009 |

OTHER PUBLICATIONS

Japanese Office Action dated Dec. 13, 2016 issued in JP 2016-553040.
Extended Supplementary European Search Report dated Oct. 18, 2018 in European Patent Application No. 15 88 5563.5.

* cited by examiner

TREATMENT INSTRUMENT

This application is a continuation based on Japanese Patent Application No. 2015-051290, filed on Mar. 13, 2015, and PCT/JP2015/081303, filed on Nov. 6, 2015. The contents of both the United States Patent Application and the PCT Application are incorporated herein by reference.

TECHNICAL FIELD

The present invention relates to a treatment instrument.

BACKGROUND ART

In the related art, in a medical field, as a treatment instrument in which a treatment unit treating for a living body tissue is arranged in a distal end of an insertion unit to be inserted into a body cavity, for example, a treatment instrument which captures a lesion such as a polyp by a snare loop is disclosed (refer to Japanese Unexamined Patent Application, First Publication No. H11-123198, Japanese Unexamined Patent Application, First Publication No. 2000-083964, and Japanese Unexamined Patent Application, First Publication No. H08-71082).

The snare loop (wire) used for each treatment instrument disclosed in Japanese Unexamined Patent Application, First Publication No. H11-123198, Japanese Unexamined Patent Application, First Publication No. 2000-083964, and Japanese Unexamined Patent Application, First Publication No. H08-71082 has a hexagonal shape which has a first bending portion, a second bending portion, and a third bending portion in the order from a distal end side of the snare loop. A proximal end side of the snare loop is tied by a connection pipe and the snare loop is inserted into a sheath so as to be advanced and retracted.

In any snare loop disclosed in Japanese Unexamined Patent Application, First Publication No. H11-123198, Japanese Unexamined Patent Application, First Publication No. 2000-083964, and Japanese Unexamined Patent Application, First Publication No. H08-71082, the length from the third bending portion to the connection pipe is the longest among a length from the first bending portion to the second bending portion, a length from the second bending portion to the third bending portion, and a length from the third bending portion to a connection pipe. In this manner, the snare loop can capture not only a small polyp but also a big polyp. It is possible to restrain operation resistance when the snare loop is pulled into the sheath.

SUMMARY OF INVENTION

According to a first aspect of the present invention, a treatment instrument includes: a sheath which has a longitudinal axis; and a wire which has a loop portion that has a loop shape in a distal end of the wire, that is inserted into the sheath so as to be advanced and retracted, and that has a first bending portion bent to protrude toward an outside of from the loop shape, a pair of second bending portions, and a pair of third bending portions, in an order from the distal end of the wire toward a proximal end of the wire. In the loop portion, a length of a second region from the pair of second bending portions to the pair of third bending portions is longer than a length of a first region from the first bending portion to the pair of second bending portions and a length of a third region from the pair of third bending portions to the proximal end of the loop portion. An angle formed inside the loop portion between the first region and the second region is equal to or smaller than an angle formed on the distal end side of the wire between the first region and the longitudinal axis. A maximum dimension of the loop portion in a direction orthogonal to the longitudinal axis in a state where half of a total length of the loop portion in a direction of the longitudinal axis of the loop portion is pulled into the sheath is 40% to 60% of a maximum dimension of the loop portion in the orthogonal direction in a state where the whole loop portion protrudes from a distal end of the sheath.

According to the treatment instrument in a second aspect of the present invention, in the above-described first aspect, a length between the pair of second bending portions arranged on both sides of the longitudinal axis is longer than a length between the pair of third bending portions arranged on both sides the longitudinal axis.

According to the treatment instrument in a third aspect of the present invention, in the above-described first aspect, in the loop portion, a length of a wire of the third region may be longer than a length of the first region.

According to the treatment instrument in a fourth aspect of the present invention, in the above-described first aspect, the third region may be bent to protrude toward an inside of the loop portion.

DESCRIPTION OF EMBODIMENTS

First Embodiment

A treatment instrument according to a first embodiment of the present invention will be described with reference to FIGS. 1 to 8.

Figure 1:
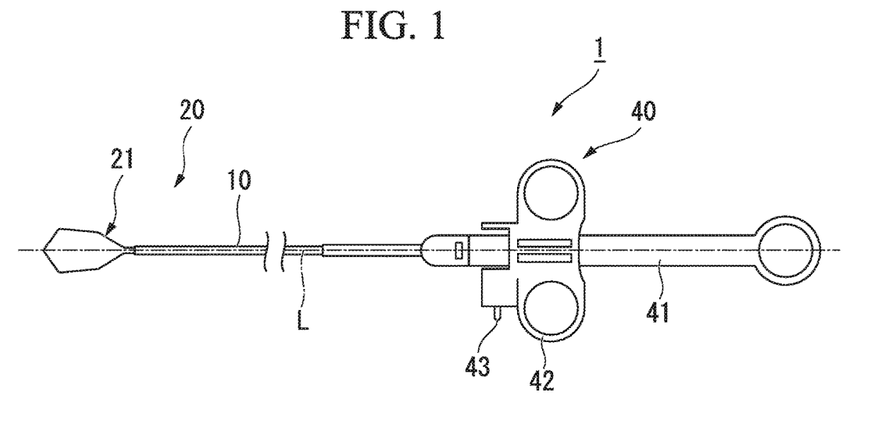
FIG. 1 is an overall view of a treatment instrument according to a first embodiment of the present invention.

As shown in FIG. 1, a treatment instrument 1 according to the present embodiment includes a sheath 10, a wire 20, and an operation unit 40.

The sheath 10 has a longitudinal axis L, and is inserted into a body cavity. In addition, the sheath 10 is configured to include an insulating material, and is formed of, for example, an insulating resin. The sheath 10 is formed of a flexible material so as to be advanced and retracted inside a channel of an endoscope having a shape extending along bent luminal tissues inside the body cavity.

Figure 2:
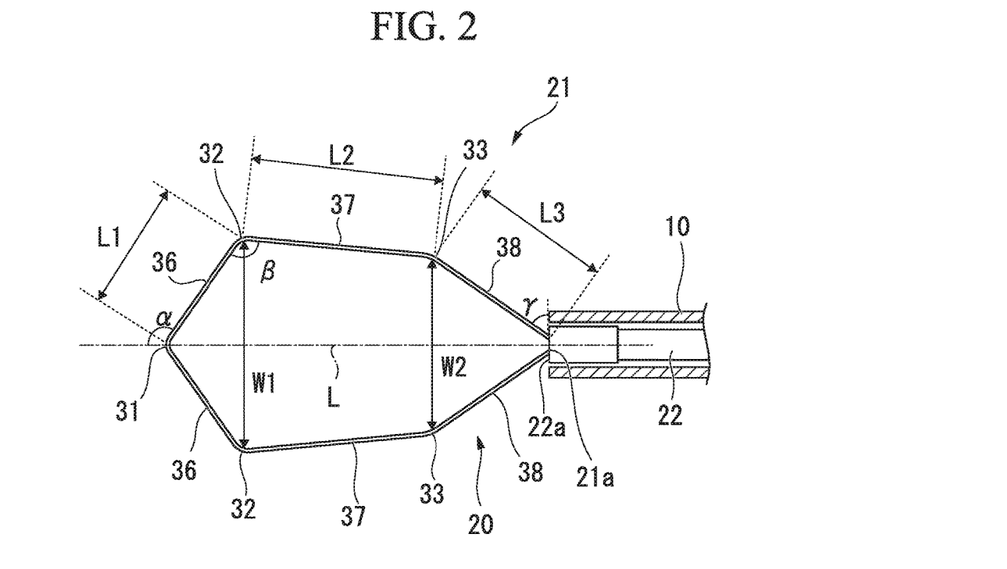
FIG. 2 is a view illustrating a loop portion of the treatment instrument in FIG. 1.

The wire 20 is inserted into the sheath 10 so as to be advanced and retracted. As shown in FIG. 2, the wire 20 includes a loop portion 21 on a distal end side, and an operation wire 22 on a proximal end side.

The wire 20 is conductive, and enables a high frequency current to pass through the wire 20.

The loop portion 21 has a first bending portion 31 which is bent to protrude toward the outside of a loop shape formed by the loop portion 21 itself, a pair of second bending portions 32, and a pair of third bending portions 33 in the order from the distal end side of the wire 20 toward the proximal end side of the wire 20.

The loop portion 21 has a first region 36 between the first bending portion 31 and the second bending portion 32, a second region 37 between the second bending portion 32 and the third bending portion 33 which are adjacent to each other, and a third region 38 between the third bending portion 33 and a proximal end 21a of the loop portion 21 which are adjacent to each other.

The loop portion 21 forms a substantially hexagonal loop which is symmetrically formed by interposing the longitudinal axis L.

Hereinafter, since the loop portion 21 is symmetrically formed by interposing the longitudinal axis L, a shape on one side (upper side in the drawing) will be described.

In the loop portion 21, a length L2 of the second region 37 is longer than a length L1 of the first region 36 and a length L3 of the third region 38. In addition, in the loop portion 21, the length L3 of the third region 38 is longer than the length L1 of the first region 36.

An angle β formed inside the loop portion 21 between the first region 36 and the second region 37 is smaller than an angle α formed in the distal end side (outside the loop) between the first region 36 and the longitudinal axis L. For example, the angle β is 100 degrees to 140 degrees. In a case where the angle α is equal to the angle β, the pair of second regions 37 is arranged so as to be parallel to each other. However, according to the present embodiment, since the angle β is smaller than the angle α, the pair of second regions 37 is in a nonparallel state. The loop portion 21 is formed so that a length W1 between the pair of second bending portions 32 arranged on both sides interposing the longitudinal axis L is longer than a length W2 between the pair of third bending portions 33 arranged on both sides interposing the longitudinal axis L. In this manner, the second region 37 is inclined in a direction closer to the longitudinal axis L from the second bending portion 32 toward the third bending portion 33. As a result, the angle formed between the second region 37 and the third region 38 becomes larger. Accordingly, an angle γ formed between a distal end surface 22a of the operation wire 22 and the third region 38 is larger than an angle formed in a case where the pair of second regions 37 is arranged so as to be parallel to each other.

As shown in FIG. 1, the operation unit 40 has an operation unit body 41 connected to the proximal end portion of the sheath 10, a slider 42 attached to the operation unit body 41, and a connector 43.

The operation wire 22 is connected to the slider 42. In this manner, the slider 42 is caused to move forward to and rearward from the operation unit body 41, thereby causing the wire 20 to move forward to and rearward from the sheath 10. According to the present embodiment, if the slider 42 is caused to move forward to the operation unit body 41, the loop portion 21 protrudes from the distal end of the sheath 10. If the slider 42 is caused to move rearward from the operation unit body 41, the loop portion 21 is accommodated inside the sheath 10.

The connector 43 can be connected to a high frequency power supply device (not shown), and can supply a high frequency current to the operation wire 22. The operation wire 22 is electrically connected to the loop portion 21. Accordingly, the high frequency current supplied from the high frequency power supply device is transmitted to the loop portion 21 via the operation wire 22.

Next, an operation of the treatment instrument 1 according to the present embodiment when excising a polyp bulging from an epithelium of a living body will be described.

First, although not shown, an endoscope is inserted into a body cavity by using a known manual skill. The distal end of the endoscope is guided to a target area to be treated, thereby capturing the polyp which is the target area within a visible field of the endoscope.

Figure 3:
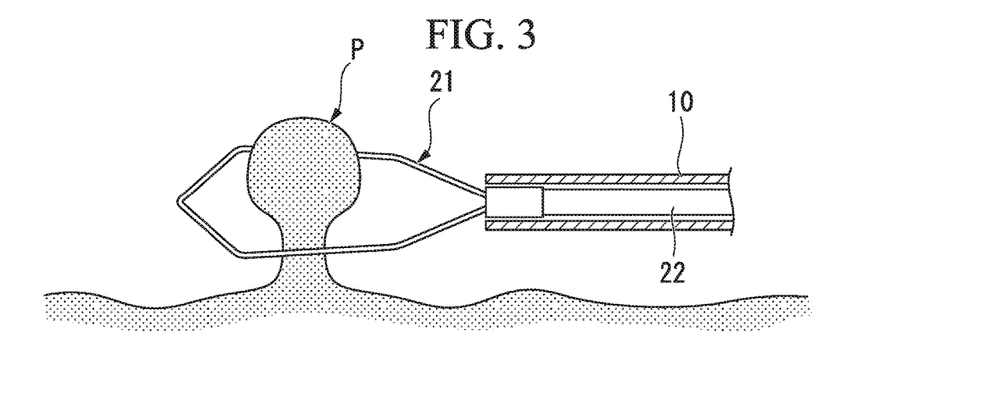
FIG. 3 is a view for describing an operation of the treatment instrument in FIG. 1.

An operator inserts the treatment instrument 1 into the endoscope, and is caused to protrude from the endoscope. Thereafter, the operator causes the slider 42 of the operation unit 40 shown in FIG. 1 to slide to the distal end side with respect to the operation unit body 41. The operation wire 22 connected to the slider 42 is pressed toward the distal end side with respect to the sheath 10 and is moved to the distal end of the sheath 10. The whole loop portion 21 protrudes from the distal end of the sheath 10, and the loop portion 21 is deformed by a restoring force using its own elasticity so as to be open in a hexagonal shape (first state). In a case where a size of the polyp is big (for example, approximately 10 mm), while the loop portion 21 is fully opened, the operator hangs the loop portion 21 on a polyp P as shown in FIG. 3.

Subsequently, the operator causes the slider 42 of the operation unit 40 to slide to the proximal side with respect to the operation unit body 41. In this manner, the proximal end side of the loop portion 21 is pulled into the sheath 10, and a root of the polyp P is bound by the loop portion 21.

Next, the operator operates the high frequency power supply device so as to supply the high frequency current to the treatment instrument 1. The high frequency current is supplied to the loop portion 21. The operator excises the polyp P while cauterizing the polyp P bound by the loop portion 21.

Figure 4:
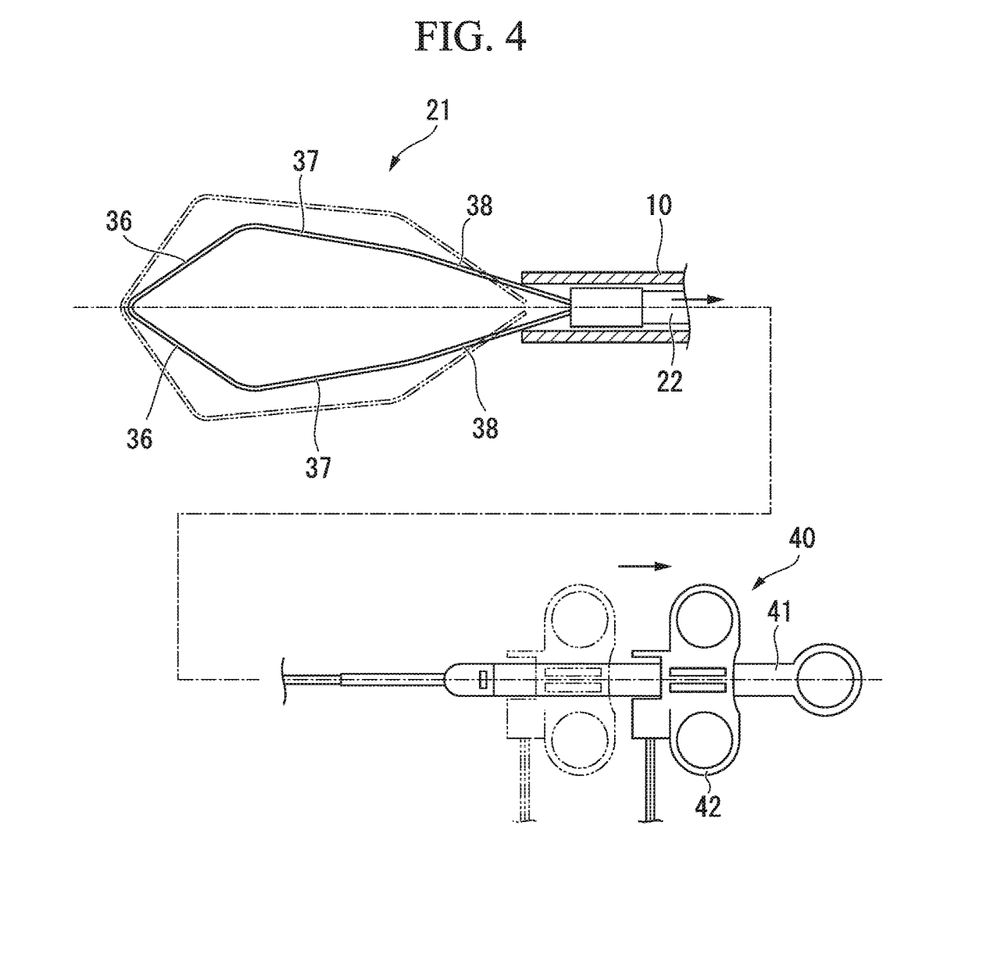
FIG. 4 is a view for describing an operation of the treatment instrument in FIG. 1.
Figure 5:
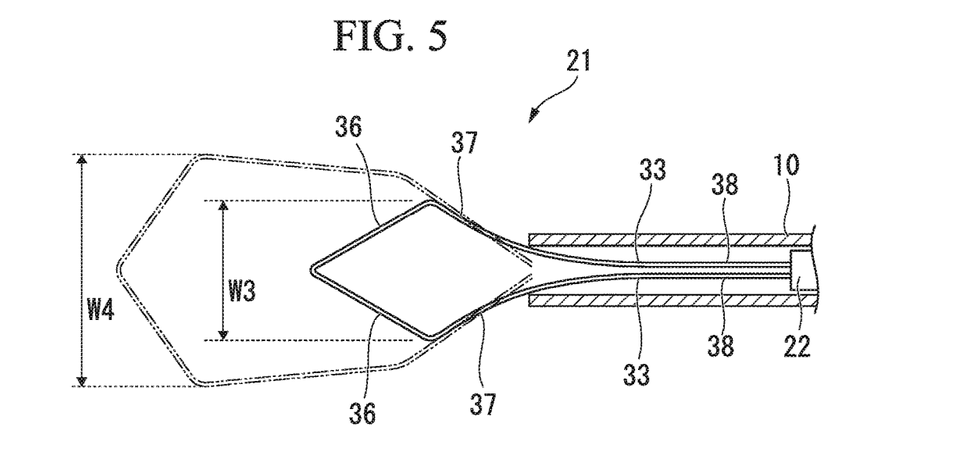
FIG. 5 is a view for describing an operation of the treatment instrument in FIG. 1.

In a case where the size of the polyp is small (for example, approximately 5 mm), the operator causes the slider 42 of the operation unit 40 to slide to the proximal end side with respect to the operation unit body 41 from a state where the whole loop portion 21 protrudes from the distal end of the sheath 10 as shown in FIG. 1. The operator starts to pull a portion of the third region 38 as shown in FIG. 4. At this time, the proximal end side of the loop portion 21 is gradually pulled into the sheath 10. Furthermore, if the slider 42 is caused to slide to the proximal end side, as shown in FIG. 5, the third region 38, the third bending portion 33, and a part of the second region 37 are sequentially accommodated inside the sheath 10, thereby causing the loop portion 21 to have a diamond shape (second state).

In the second state, particularly in a state where approximately the half of the total length in the direction of the longitudinal axis L of the loop portion 21 is pulled into the sheath 10, a maximum dimension W3 of th loop portion 21 in an orthogonal direction orthogonal to the longitudinal axis L is 40% to 60% of a maximum dimension W4 of the loop portion 21 in the orthogonal direction in the first state. According to the present embodiment, the dimension W3 is 60% of the dimension W4.

Figure 6:
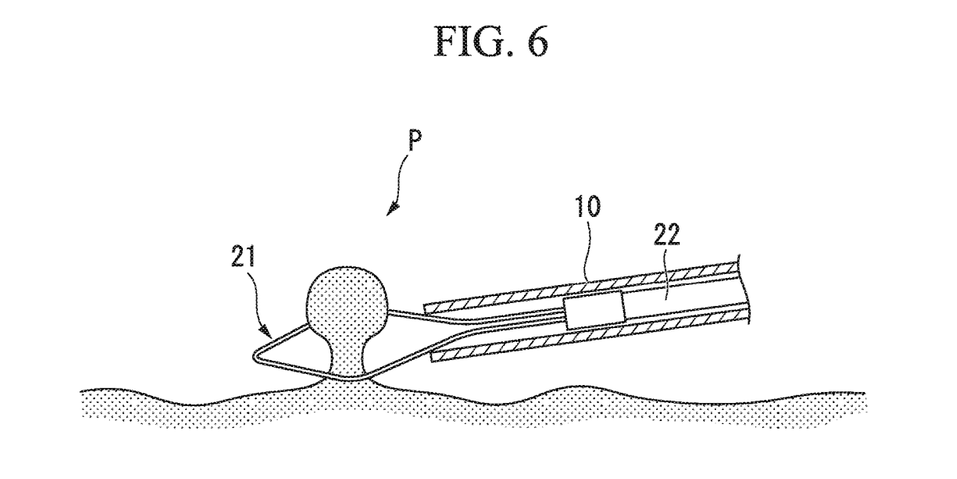
FIG. 6 is a view for describing an operation of the treatment instrument in FIG. 1.

As shown in FIG. 6, the operator brings the loop portion 21 into the second state, and hangs the loop portion 21 on the polyp P. Thereafter, similarly to the above-described case where the size of the polyp is big, the operator supplies the high frequency current to the loop portion 21, and excises the polyp P bound by the loop portion 21.

Figure 7:
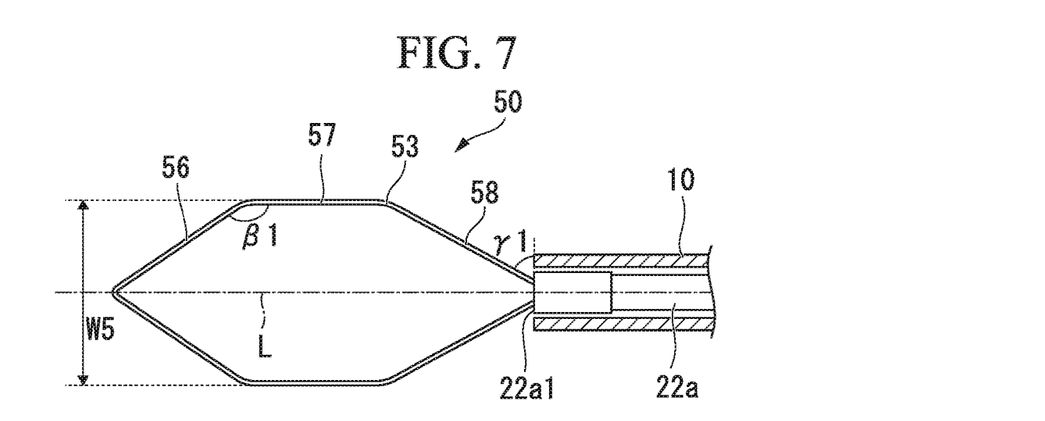
FIG. 7 is a view illustrating a treatment instrument in the related art.

According to a treatment instrument in the related art, in order to enable an operator to capture not only a small polyp but also a big polyp, as shown in FIG. 7, a loop portion 50 is formed so that the length of a first region 56 and the length of a third region 58 are longer than the length of a second region 57. In a case where the total length in the direction of the longitudinal axis L of the loop portion 50 is equal to that of the loop portion 21 of the treatment instrument 1 according to the present embodiment, the loop portion 50 has a shape in which an opening width W5 of the loop portion 50 is shorter than the total length in the direction of the longitudinal axis L of the loop portion 50 compared to the present embodiment.

Figure 8:
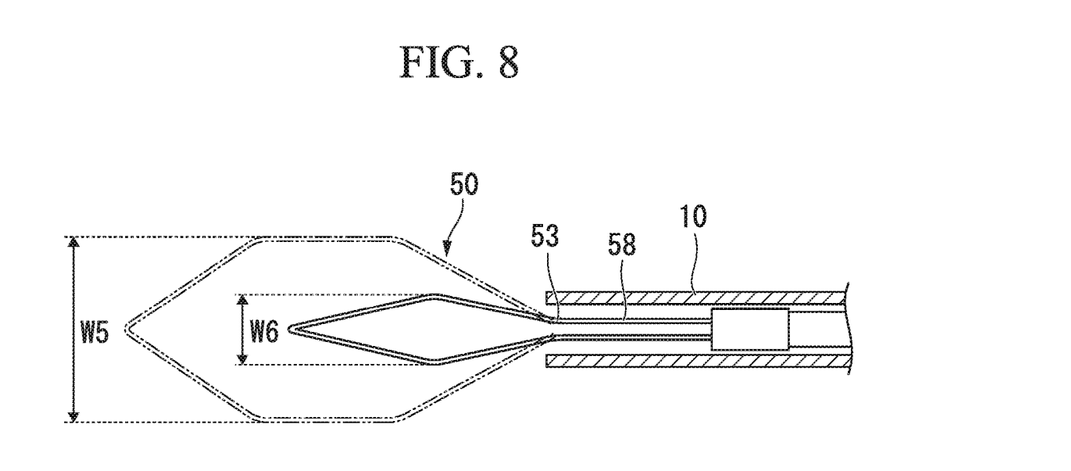
FIG. 8 is a view illustrating a treatment instrument in the related art.

In addition, due to a relationship among the lengths of the first region 56, the second region 57, and the third region 58 which are described above, an angle β1 formed between the first region 56 and the second region 57 becomes larger than the angle β of the loop portion 21. Therefore, when the third region 58 begins to be pulled into the sheath 10, the loop portion 50 rapidly shrinks as shown in FIG. 8.

A dimension W6 when a third bending portion 53 is also accommodated inside the sheath 10 (the third bending portion 53 and the third region 58 are accommodated inside the sheath 10) decreases to approximately 30% of the dimension W5 of the loop portion 50 in the orthogonal direction in a state the whole loop portion 50 shown in FIG. 7 protrudes from the distal end of the sheath 10.

Therefore, according to the treatment instrument in the related art, in a state where the whole loop portion 50 protrudes from the sheath 10, the total length in the direction of the longitudinal axis L of the loop portion 50 with respect to the opening width W5 is longer than the total length in the direction of the longitudinal axis L of the loop portion 21 with respect to the opening width W4 in the present embodiment. Consequently, even when the big polyp is captured, a normal tissue in the vicinity of the polyp also enters the inside of the loop portion 50. In addition, if the third region 58 is pulled into the sheath 10 in order to capture the small polyp, the loop portion 50 collapses, and the size rapidly becomes smaller. Thus, the polyp is less likely to be captured. Therefore, If the small polyp is captured in a state where the whole loop portion 50 protrudes from the sheath 10, a larger amount of the normal tissue in the vicinity also enters the inside of the loop portion 50 compared to the case where the big polyp is captured.

In a case where the angle β1 formed between the first region 56 and the second region 57 of the treatment instrument in the related art is set to an angle (angle smaller than the angle β1) which is equal to the angle β formed by the loop portion 21 of the treatment instrument according to the present embodiment, an angle γ1 formed between a distal end surface 22a1 of an operation wire 22a and the third region 58 becomes smaller. Accordingly, an opening width W6 of the loop when the third region 58 is pulled into the sheath 10 rapidly becomes smaller compared to the above-described case.

According to the treatment instrument 1 in the present embodiment, the length L2 of the second region 37 is longer than both of the length L1 of the first region 36 and the length L3 of the third region 38. Accordingly, the angle β corresponding to the angle β1 of the treatment instrument in the related art is smaller than the angle β1. Therefore, the loop portion 21 is not rapidly pulled into the sheath 10, and gradually shrinks, thereby enabling the loop portion 21 to be formed in a diamond shape.

In addition, the dimension W3 when the loop portion 21 is in the second state is 60% of the dimension W4 when the loop portion 21 is in the first state. Accordingly, even if the loop portion 21 is pulled into the sheath 10 until the loop portion 21 is brought into the second state, the loop does not excessively become smaller. In this manner, in a case of the big polyp, the loop portion 21 can be adjusted in the first state and the polyp P is capable of being bound. In a case of the small polyp, the loop portion 21 can be adjusted in the second state and the polyp P is capable of being bound. Therefore, depending on the size of the polyp P, it is possible to properly change the loop size of the loop portion 21.

As a result, even if the total length in the direction of the longitudinal axis L of the loop portion 21 with respect to opening width W4 is not longer than that of the loop portion 50 in the related art, it is possible to suitably capture the polyps P having respectively different sizes. As a result, it is possible to prevent the normal tissue in the vicinity of the polyp P from entering the inside of the loop portion 21. In this manner, it is possible to suitably capture a lesion.

Furthermore, the loop portion 21 is not rapidly pulled into the sheath 10. Accordingly, depending on the size of the polyp P, the size of the loop portion 21 can be adjusted by pulling the third region 38 into the sheath 10.

Furthermore, the loop portion 21 is formed so that the angle α is larger than the angle β. That is, the second region 37 is inclined in the direction closer to the longitudinal axis L from the second bending portion 32 toward the third bending portion 33. Accordingly, the angle γ formed between the distal end surface 22a of the operation wire 22 and the third region 38 is large. In this manner, operation resistance is minimized when the operation wire 22 is pulled into the sheath 10. Therefore, the loop portion 21 can be smoothly accommodated inside the sheath 10.

In addition, the length L3 of the third region 38 is longer than the length L1 of the first region 36. Accordingly, compared to a case where the length L3 of the third region 38 is shorter than the length L1 of the first region 36, the angle α can be minimized. In this manner, since the first region 36 rises from the longitudinal axis L (a rising angle between the first region 36 and the longitudinal axis L formed inside of the loop portion 21 is large), even if the loop portion 21 is pulled into the sheath 10, an advantageous effect is achieved in that the loop portion 21 is less likely to collapse.

A configuration is adopted in which the high frequency current is caused to flow into the loop portion 21 of the treatment instrument 1. However, a configuration may be adopted in which the high frequency current is not caused to flow into the loop portion 21.

The angle α formed on the distal end side (outside the loop) between the first region 36 and the longitudinal axis L is set to be larger than the angle β formed inside the loop portion 21 between the first region 36 and the second region 37. However, the angle α and the angle β may be equal to each other.

The length L3 of the third region 38 is set to be longer than the length L1 of the first region 36. However, the length L1 of the first region 36 may be longer than the length L3 of the third region 38.

Second Embodiment

Figure 10:
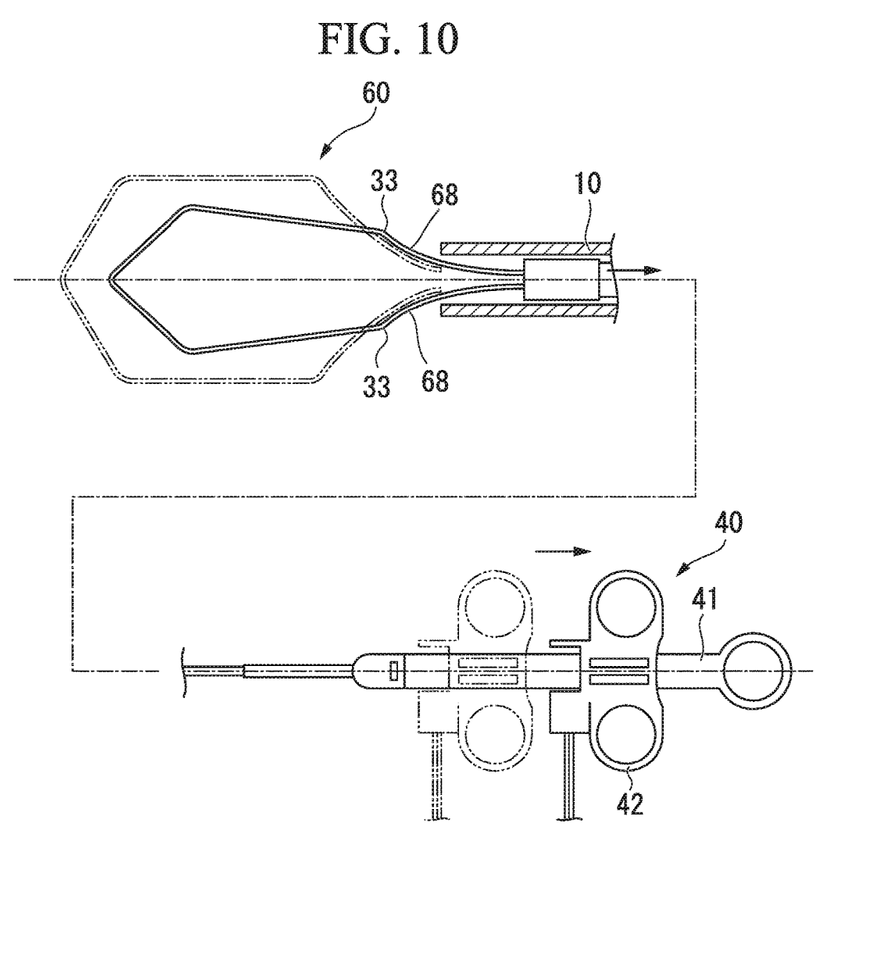
FIG. 10 is a view for describing an operation of the treatment instrument in FIG. 9.
Figure 11:
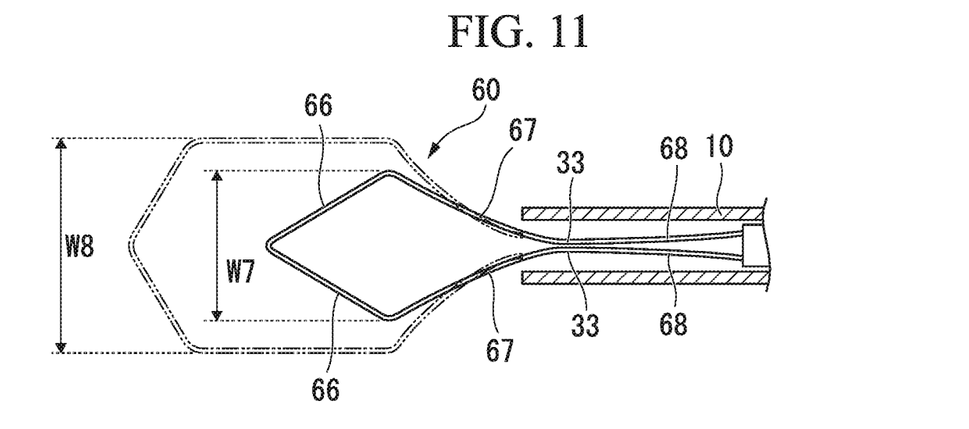
FIG. 11 is a view for describing an operation of the treatment instrument in FIG. 9.

A second embodiment according to the present invention will be described with reference to FIGS. 9 to 11.

A treatment instrument according to the present embodiment has a configuration of a loop portion which is different from that according to the first embodiment.

In the following description, the same reference numerals will be given to configuration elements common to those described above, and thus, repeated description will be omitted.

Instead of the pair of second regions 37 according to the first embodiment, a loop portion 60 includes a pair of second regions 67. Instead of the pair of third regions 38 according to the first embodiment, the loop portion 60 includes a pair of third regions 68.

The third region 68 is bent to protrude toward the inside of the loop. In this manner, the angle γ formed between the distal end surface 22a of the operation wire 22 and the third region 68 is larger than that when the third region 68 is in a linear state.

In addition, the angle α formed on the distal end side (outside the loop) between the first region 36 and the longitudinal axis L is equal to the angle β formed inside the loop portion 60 between the first region 36 and the second region 67. That is, the pair of second regions 67 is arranged so as to be parallel to each other on both sides interposing the longitudinal axis L.

In the loop portion 60, the third region 68 is bent. However, the loop portion 60 forms a loop having a substantially hexagonal shape which is symmetrically formed by interposing the longitudinal axis L.

Next, a method will be described in which a polyp bulging from an epithelium of a living body is excised by using the treatment instrument according to the present embodiment.

Figure 9:
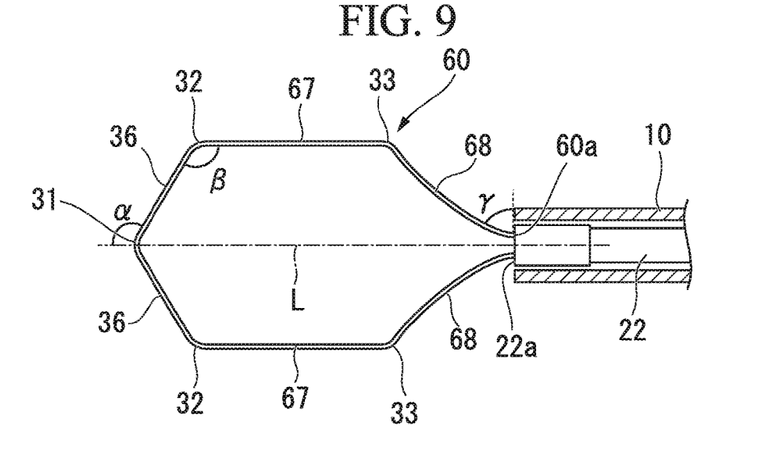
FIG. 9 is a view illustrating a loop portion of a treatment instrument according to a second embodiment of the present invention.

As shown in FIG. 9, in a state where the whole loop portion 60 protrudes from the distal end of the sheath 10 (first state), an operator causes the slider 42 of the operation unit 40 to slide to the proximal end side with respect to the operation unit body 41. As shown in FIG. 10, the operator starts to pull a portion of the third region 68. At this time, since the third region 68 is bent to protrude toward the inside of the loop, the proximal end side of the loop portion 60 is gradually pulled into the sheath 10. Furthermore, if the slider 42 is caused to slide to the proximal end side, as shown in FIG. 11, the third region 68, the third bending portion 33, and a portion of the second region 67 are sequentially accommodated inside the sheath 10, thereby causing the loop portion 60 to have a diamond shape (second state). Then, similarly to the first embodiment, the high frequency current is supplied to the loop portion 60, the operator excises the polyp P bound by the loop portion 60.

In the second state, particularly in a state where approximately the half of the total length in the direction of the longitudinal axis L of the loop portion 60 is pulled into the sheath 10, a maximum dimension W7 of th loop portion 60 in the orthogonal direction orthogonal to the longitudinal axis L is 40% to 60% of a maximum dimension W8 of the loop portion 60 in the orthogonal direction in the first state, similarly to the first embodiment.

According to the treatment instrument in the present embodiment, the angle γ formed between the distal end surface 22a of the operation wire 22 and the third region 68 is larger than that when the third region 68 is in a linear state. Accordingly, operation resistance is minimized when the operation wire 22 is pulled into the sheath 10. Therefore, the loop portion 60 can be smoothly accommodated inside the sheath 10.

In a state where the angle α is larger than the angle β as in the first embodiment, the third region 68 may be bent to protrude toward the inside of the loop. In addition, the third region 68 may be in a straight state as in the first embodiment, while the pair of the second regions 67 is arranged so as to be parallel to each other.

The preferred embodiments according to the present invention have been described. However, the present invention is not limited to the embodiments. Additions, omissions, substitutions, and modifications of the configurations can be made without departing from the scope of the present invention. Without being limited by the above description, the present invention is limited by the accompanying claims.

The invention claimed is:

1. A treatment instrument comprising:
   a sheath which has a longitudinal axis; and
   a wire which has a loop that has a loop shape in a distal end of the wire, the wire being inserted into the sheath so as to be advanced and retracted, the loop having:
     a pair of first wire segments each bent to protrude outward in opposite directions from the longitudinal axis of the sheath in a state where an entirety of the loop protrudes from a distal end of the sheath,
     a pair of second wire segments each bent relative to an adjacent one of the pair of first wire segments to protrude inwards towards the longitudinal axis of the sheath in a state where an entirety of the loop protrudes from the distal end of the sheath,
     and a pair of third wire segments each bent relative to an adjacent one of the pair of second wire segments to protrude inward towards the longitudinal axis of the sheath in a state where an entirety of the loop protrudes from the distal end of the sheath,
   wherein the pair of first wire segments, the pair of second wire segments and the pair of third wire segments being arranged in order from the distal end of the wire toward a proximal end of the wire,
   in the loop, a length of each of the pair of second wire segments is longer than a length of the adjacent one of the pair of first wire segments and a length of the each of the pair of second wire segments is longer than a length of an adjacent one of the pair of third wire segments,
   an angle formed on an inside of the loop between each of the pair of the first wire segments and the adjacent one of the pair of second wire segments is equal to or smaller than an angle formed on the distal end side of the wire on an outside of the loop between each of the pair of first wire segments and the longitudinal axis in a state where the whole loop portion protrudes from the distal end of the sheath and an angle between each of the pair of second wire segments and the adjacent one of the pair of third wire segments on the inside of the loop being less than 180 degrees,
   a maximum dimension of the loop in a direction orthogonal to the longitudinal axis in a state where half of a total length of the loop in a direction of the longitudinal axis of the loop is pulled into the sheath is 40% to 60% of a maximum dimension of the loop in the orthogonal direction in a state where the whole loop protrudes from the distal end of the sheath, and
   an entirety of each one of the pair of second wire segments is formed linearly without a bend in the state where the entirety of the loop protrudes from the distal end of the sheath.

2. The treatment instrument according to claim 1, wherein a length between each of the pair of second wire segments arranged on both sides of the longitudinal axis is longer than a length between each of the pair of adjacent third wire segments arranged on both sides of the longitudinal axis.

3. The treatment instrument according to claim 1, wherein in the loop, the length of each of the pair of third wire segments is longer than the length of each of the pair of first wire segments.

4. The treatment instrument according to claim 1, wherein in the state where the entirety of the loop protrudes from the distal end of the sheath, a maximum opening width dimension of the loop in a direction intersecting with the longitudinal axis is defined by a length between the pair of second wire segments arranged on both sides of the longitudinal axis.

5. The treatment instrument according to claim 1, wherein in the state where the entirety of the loop protrudes from the distal end of the sheath, each one of the pair of second wire segments approach the longitudinal axis as each one of the pair of second wire segments extend toward the adjacent one of the pair of third wire segments.

* * * * *